United States Patent
Neumann et al.

(10) Patent No.: US 11,291,675 B2
(45) Date of Patent: Apr. 5, 2022

(54) 6'-SIALYLLACTOSE FOR USE IN THE TREATMENT OF HEARING LOSS

(71) Applicant: Rheinische Friedrich-Wilhelms-Universität Bonn, Bonn (DE)

(72) Inventors: Harald Neumann, Bonn (DE); Christine Klaus, Montabaur (DE); Anahita Shahraz, Bonn (DE)

(73) Assignee: Rheinische Friedrich-Wilhelms-Universität Bonn, Bonn (DE)

( * ) Notice: Subject to any disclaimer, the term of this patent is extended or adjusted under 35 U.S.C. 154(b) by 0 days.

(21) Appl. No.: 16/770,402

(22) PCT Filed: Dec. 7, 2018

(86) PCT No.: PCT/EP2018/083920
§ 371 (c)(1),
(2) Date: Jun. 5, 2020

(87) PCT Pub. No.: WO2019/115374
PCT Pub. Date: Jun. 20, 2019

(65) Prior Publication Data
US 2020/0289537 A1    Sep. 17, 2020

(30) Foreign Application Priority Data

Dec. 12, 2017 (EP) ..................... 17206770

(51) Int. Cl.
A61P 27/16    (2006.01)
A61K 31/702    (2006.01)
A61K 31/7016    (2006.01)

(52) U.S. Cl.
CPC ........ *A61K 31/7016* (2013.01); *A61K 31/702* (2013.01); *A61P 27/16* (2018.01)

(58) Field of Classification Search
CPC ........................... A61K 31/7016; A61P 27/16
See application file for complete search history.

(56) References Cited

U.S. PATENT DOCUMENTS

2015/0342974 A1    12/2015  Chow et al.
2019/0030053 A1    1/2019   Kang

FOREIGN PATENT DOCUMENTS

| WO | WO 2009/059996 A1 | 5/2009 |
| WO | WO 2016/139328 A1 | 9/2016 |
| WO | WO 2017/123066 A1 | 7/2017 |
| WO | WO 2017/198276 A1 | 11/2017 |

OTHER PUBLICATIONS

6'-Sialyllactose, PubChem, 19 pages, available at https://pubchem.ncbi.nlm.nih.gov/compound/6_-Sialyllactose; obtained Jun. 30, 2021 (Year: 2021).*
International Search Report dated Mar. 13, 2019 from corresponding International Application No. PCT/EP2018/083920.
European Search Report dated Jun. 6, 2018 from corresponding European Application No. EP 17 20 6770.
International Written Opinion dated Mar. 13, 2019 from corresponding International Application No. PCT/EP2018/083920.

* cited by examiner

*Primary Examiner* — Bahar Craigo
(74) *Attorney, Agent, or Firm* — Davidson, Davidson & Kappel, LLC

(57) ABSTRACT

The present invention relates to 6'-sialyllactose and/or pharmaceutically acceptable salts thereof for use in the treatment of a disease selected from hearing loss and hearing loss—associated tinnitus.

15 Claims, 3 Drawing Sheets

6'-SIALYLLACTOSE FOR USE IN THE TREATMENT OF HEARING LOSS

Figure 1:
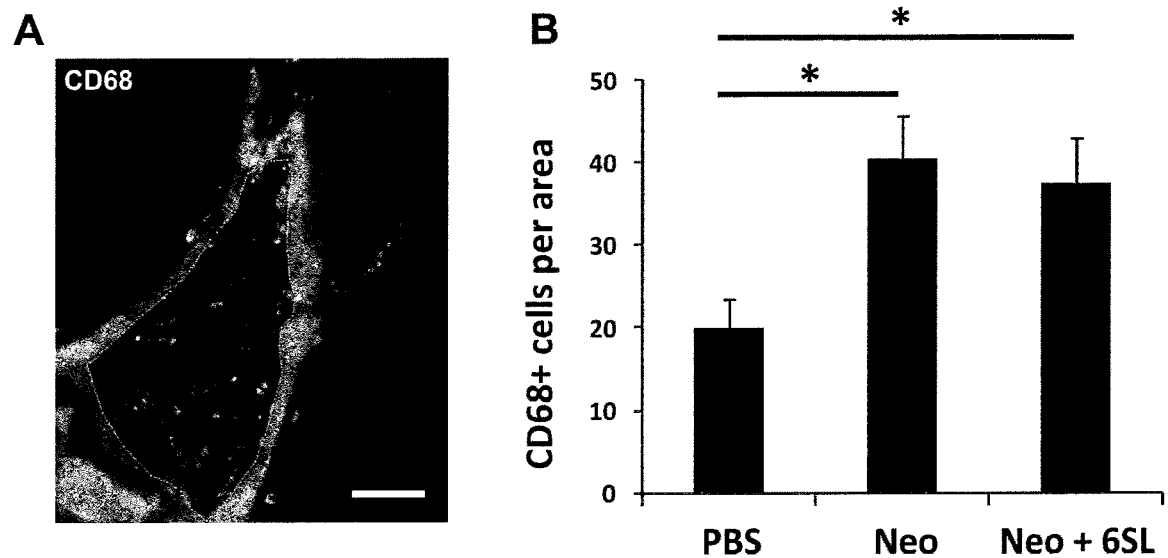

This application is a U.S. national phase application under 35 U.S.C. of § 371 of International Application No. PCT/EP2018/083920, Dec. 7, 2018, which claims priority of European Patent Application No. EP 17 206 770.4, filed Dec. 12, 2017, the disclosures of which are hereby incorporated by reference herein.

The present invention relates to the treatment of hearing loss.

Acquired, non-hereditary sensorineural hearing loss affects about half of the estimated 700 million cases of debilitating hearing loss worldwide. Acquired hearing loss can be a consequence of infectious diseases or of non-infections origin. The three major causes of acquired, non-infectious hearing loss are noise exposure, drug-induced ototoxicity and age. Most of the cases of hearing loss arise from injury to the sensorineural system of the inner ear and the associated nerves. Sensorineural hearing loss occurs due to lesions on the hair cells of the cochlear organ of Corti (inner ear) and/or of the cochlear nerve. Hair cells of the cochlea are specialized neuroepithelial cells required for the transduction of vibrational force into the perception of hearing. These specialized neuroepithelial cells are post-mitotic, terminally differentiated cells in mammals and thus, cannot be replaced by regeneration if they are lost. The molecular events leading to noise-induced and drug-induced ototoxicity, and age-related hearing loss are complex and not fully understood. A curative or protective treatment for degenerative diseases of the auditory system does not exist and most therapies are therefore symptomatic. For example, Wong and Ryan in "Mechanisms of sensorineural cell damage, death and survival in the cochlea" (Front. Aging Neurosci., 7:58, 2015) describe intracellular mechanisms of hair cell loss and therapeutic interventions including various antioxidants, anti-apoptotics, and pro-inflammatory cytokine inhibitors.

Sialyllactose is one of the acidic human milk oligosaccharides. The sialic acid of the human sialyllactose only contains N-acetylneuraminic acid and no N-glycolylneuraminic acid. The sialic acid group shows two different linkages, thus forming 6'-sialyllactose and 3'-sialyllactose. Human milk oligosaccharides including sialyllactose have been suggested as potential therapy in several human disorders. US 2015/0342974 A1 discloses a nutritional composition comprising human milk oligosaccharides comprising at least one human milk oligosaccharide selected from lacto-N-neotetraose and 2'-fucosyllactose, and optionally further oligosaccharides including sialyllactose in providing a neuroprotective effect in the central nervous system. U.S. Pat. No. 9,283,240 B2 describes human milk oligosaccharides including sialyllactose for reducing inflammation in infants, toddlers and children. WO 2016/139328 discloses nutritional compositions comprising oligosaccharides for the treatment of infections or inflammations of the lower respiratory tract or the ear in infants and children.

Although increasing details of the complex mechanisms of inner ear disorders have been identified, treatments that can ameliorate the damage to the inner ear pathology and can reduce the impact of sensorineural hearing loss remain difficult, and it is nearly impossible to predict if a compound can prevent loss of hair cells or sensory neurons of the cochlea.

Therefore, the object underlying the present invention was to provide compounds that are usable in the treatment of hearing loss.

The problem is solved by 6'-sialyllactose and/or pharmaceutically acceptable salts thereof for use in the treatment of a disease selected from hearing loss and hearing loss-associated tinnitus.

Surprisingly, it was found that 6'-sialyllactose can be used for the prevention and/or treatment of hearing loss, particularly of acquired, non-infectious hearing loss. It was found that for example antibiotic-induced damage of the auditory system could be treated using 6'-sialyllactose in mice in vivo. Subcutaneous application of 6'-sialyllactose reduced a neomycin-induced loss of hair cells in the middle layer of the cochlea of the mice. Likewise, 6'-sialyllactose reduced the neomycin-induced loss of the sensory neurons in the spiral ganglion of the auditory system of the mice.

The term "6'-sialyllactose" according to the invention refers to a glycan comprising three sugar monomers according to general formula (1) as given as follows:

$$\text{Neu5Ac-}\alpha(2\rightarrow 6)\text{-Gal-}\beta(1\rightarrow 4)\text{-Glc} \quad (1)$$

wherein:
Neu5Ac is N-acetylneuraminic acid,
Gal is D-galactose and
Glc is D-glucose.

N-acetylneuraminic acid (Neu5Ac) is linked to galactose (Gal) by alpha (2→6) linkage and the galactose is linked to glucose (Glc) by beta (1→4) linkage, forming Neu5Ac-α-2-6-Gal-β1-4-Glc.

The monosaccharide N-acetylneuraminic acid (Neu5Ac) is denoted (4S,5R,6R)-5-acetamido-2,4-dihydroxy-6-[(1R,2R)-1,2,3-trihydroxypropyl]oxane-2-carboxylic acid according to the IUPAC nomenclature. The monosaccharide D-Galactose (Gal) is denoted (3R,4S,5R,6R)-6-(hydroxymethyl)oxane-2,3,4,5-tetrol according to the IUPAC nomenclature. The monosaccharide D-gluco se (Glc) is denoted (3R,4S,5S,6R)-6-(hydroxymethyl)oxane-2,3,4,5-tetrol according to the IUPAC nomenclature.

The term "hearing loss" according to the invention refers to a sensorineural hearing loss, a loss of hearing, including partial or total deafness, due to a disorder of the sensory mechanism of the acoustic perception, nerve or central nervous pathways. The sensorineural hearing loss particularly can be a cochlear sensorineural hearing loss that is specific to the cochlea. The untreated sensorineural hearing loss (SNHL) is generally permanent and can be mild, moderate, severe, profound, or total.

The term "hearing loss-associated tinnitus" according to the invention refers to a hearing loss that is small or only affects a narrow band of frequencies as a consequence of a minor injury to the inner ear so that it results in an experienced tinnitus. Hearing loss-associated tinnitus is often the first sign of mild hearing loss.

The term "treatment" according to the invention particularly refers to preventing the progression of hearing loss or delaying the onset of a pre-clinically evident stage of a clinical condition or disorder. The term "treatment" is to be understood as meaning that the 6'-sialyllactose can also be applied before symptoms of the hearing loss are manifest, while partial loss of hearing distinct frequencies might be already evident. As 6'-sialyllactose is able to reduce neomycin-induced loss of sensory neurons, hearing can be improved, and hearing loss reduced. The amount of hearing restored by administration of 6'-sialyllactose may vary among subjects. In other examples, hearing may not be restored, but instead be stabilised to prevent or slow the progression of hearing loss. The term "treatment" thus, also refers to stabilising symptomatic hearing, thus, preventing further hearing loss.

Sensorineural hearing loss may be caused by genetic mutations, but often is non-hereditary and occurs as a consequence of damaged hair cells or auditory nerves. If such damage is due to external causes of damage, the hearing loss is denoted acquired hearing loss. The acquired hearing loss can be related to an infection or of non-infectious origin. In embodiments, the disease is selected from acquired hearing loss and acquired hearing loss-associated tinnitus. Autoimmune diseases for example can result in hearing loss. Preferably, the disease is selected from acquired, non-infectious hearing loss and acquired, non-infectious hearing loss-associated tinnitus. The three major causes of acquired, non-infectious hearing loss are noise exposure, drug-related ototoxicity and age. In preferred embodiments, the acquired non-infectious hearing loss is selected from the group comprising age-related hearing loss, noise-induced hearing loss and drug-induced hearing loss. Drug-induced hearing loss preferably is selected from antibiotic-induced hearing loss, chemotherapy-induced hearing loss, loop diuretic-induced hearing loss and aspirin-induced hearing loss. One of the most common causes of hearing loss is excessive exposure to noise. This problem is particularly common in loud workplaces. Noise-induced hearing loss can be caused by a one-time exposure to loud sound, as well as by repeated exposure to noise over an extended period of time. Antibiotic-induced hearing loss and hearing loss associated with chemotherapeutics is a possible side effect of such agents. For example, the chemotherapy cisplatin which is used to treat cancers such as breast, ovarian and lung cancers and a class of antibiotics known as aminoglycosides are known to cause irreversible hearing loss. However, age-related hearing loss is one of the most common forms of permanent hearing loss and deafness. In preferred embodiments, the acquired, non-infectious hearing loss is age-related hearing loss. The acquired, non-infectious hearing loss further may be associated with tinnitus. Hearing loss-associated tinnitus is often the first sign of mild hearing loss.

The 6'-sialyllactose can be free or glycosidically bound. The term "glycosidically bound" according to the invention is to be understood as meaning the 6'-sialyllactose being bound to a further saccharide molecule, or other molecules capable of forming a glycosidic bond such as amino acids. Preferably, the 6'-sialyllactose is in the form of the free glycan. The term "free" according to the invention is to be understood as meaning 6'-sialyllactose that is not bound to a further saccharide or other molecule. In preferred embodiments, the 6'-sialyllactose is free being the molecule Neu5Ac-α(2→6)-Gal-β(1→4)-Glc (1).

In further embodiments, the 6'-sialyllactose can be glycosidically bound to at least one sugar selected from the group comprising glucose, N-acetylglucosamine, N-acetylgalactosamine, galactose, fucose, mannose and xylose. The term "sugar" according to the invention is to be understood as meaning monosaccharides and disaccharides, which commonly are referred to as sugars. Advantageously, glucose, N-acetylglucosamine, N-acetylgalactosamine, galactose, fucose, mannose and xylose are essential sugars within the human body. The 6'-sialyllactose can comprise one terminal sugar molecule or be glycosidically bound to two or more sugar molecules. Further, the 6'-sialyllactose via a glycosidically bound sugar can glycosidically bind to one or more amino acids to form glycoproteins. 6'-Sialyllactose glycosidically linked to one or more sugar molecules or amino acids can result in improved pharmacokinetics. The term "amino acid" according to the invention is to be understood as meaning alpha amino acids, molecules containing both amine and carboxyl functional groups attached to the same carbon, which is called the alpha-carbon. Preferred amino acids are naturally occurring amino acids, selected from the group comprising glycine, alanine, serine, threonine, arginine, lysine, aspartic acid, glutamic acid, asparagine, glutamine, phenylalanine, tyrosine, tryptophan, leucine, valine, isoleucine, cysteine, methionine, histidine and/or proline.

The 6'-sialyllactose can be derived from natural, synthetic or bioengineered sources. Methods for the specific synthesis or bioengineering of oligo- and polysaccharides by using the monosaccharide units as precursors or appropriate genetically engineered bacteria are known to a person skilled in the art. Further, 6'-sialyllactose can be isolated from a dietary source such as whey waste streams. For examples, a dairy stream may be purified to an oligosaccharide or glycan by filtration or chromatographic methods. Conventional methods are known to those of ordinary skill in the art.

Alternatively, 6'-sialyllactose can be used in non-isolated form. In embodiments, the 6'-sialyllactose is contained in a glycan or human milk oligosaccharide composition obtained from a source of non-human origin. The term "human milk oligosaccharides" as used herein refers to oligosaccharides that are identical or very similar to oligosaccharides of the human milk, but are obtained from non-human origin. A human milk oligosaccharide composition may be derived from natural animal sources or may be recreated using synthetic or biotechnological sources. A human milk oligosaccharide composition may be derived from animal milk, for example by filtration or fractionation. Or a human milk oligosaccharide composition may contain synthesised or biotechnological produced glycans, preferably in a composition modelled according to the natural composition. Also, other mammal or synthetic or biotechnological glycan compositions may be used.

Also suitable are pharmaceutically acceptable salts of 6'-sialyllactose. The term "pharmaceutically acceptable salts" refers to salts prepared from pharmaceutically acceptable non-toxic bases or acids. A corresponding salt can be conveniently prepared from pharmaceutically acceptable non-toxic bases, including inorganic bases and organic bases. Preferred salts derived from inorganic bases include ammonium, calcium, magnesium, potassium and sodium salts. Salts derived from pharmaceutically acceptable organic non-toxic bases include salts of primary, secondary, and tertiary amines, as well as cyclic amines. Preferably, the pharmaceutically acceptable salt is selected from the group comprising sodium, potassium, calcium or magnesium salts.

A further aspect of the present invention relates to a pharmaceutical or nutritional composition comprising 6'-sialyllactose and/or pharmaceutically acceptable salts thereof as an active ingredient for use in the treatment of a disease selected from hearing loss and hearing loss-associated tinnitus. In preferred embodiments, the pharmaceutical or nutritional composition is usable in the treatment of a disease selected from acquired hearing loss and acquired hearing loss-associated tinnitus, preferably from acquired, non-infectious hearing loss and acquired, non-infectious hearing loss-associated tinnitus. In preferred embodiments, the acquired, non-infectious hearing loss is selected from the group comprising age-related hearing loss, noise-induced hearing loss and drug-induced hearing loss. Drug-induced hearing loss preferably is selected from antibiotic-induced hearing loss, chemotherapy-induced hearing loss, loop diuretic-induced hearing loss and aspirin-induced hearing loss. In preferred embodiments, the acquired hearing loss is age-related hearing loss. In further embodiments, the acquired non-infectious hearing loss is associated with tinnitus.

The 6'-sialyllactose in the pharmaceutical or nutritional composition in preferred embodiments may be present in the form of the free or glycosidically unbound form. In further embodiments, the 6'-sialyllactose in the pharmaceutical or nutritional composition may be glycosidically bound to at least one sugar selected from the group comprising glucose, N-acetylglucosamine, N-acetylgalactosamine, galactose, fucose, mannose and xylose.

The composition comprising 6'-sialyllactose can be a pharmaceutical or a nutritional composition. While 6'-sialyllactose may be used in a concentration or formulation qualifying a composition as a pharmaceutical composition, it will be understood that 6'-sialyllactose being part of mammalian animal-derived milk may be used in the form of a nutritional or dietary composition. While a manifestation of more or less severe hearing loss may call for treatment utilizing a pharmaceutical composition, treatment is equally applicable by using a nutritional composition. A treatment thus also may refer to the use of a nutritional composition.

In embodiments of the pharmaceutical or nutritional composition, the 6'-sialyllactose is contained in a glycan or human milk oligosaccharide composition. Particularly a nutritional composition may comprise 6'-sialyllactose in the form of a glycan or human milk oligosaccharide composition.

The pharmaceutical composition may be formulated for systemic application such as intravenous, subcutaneous or oral application. A pharmaceutical composition can be suitable for oral, dermal, rectal, topical, and parenteral administration. The pharmaceutical composition may be applicable via the parenteral, oral or rectal route. Parenteral administration particularly includes intratympanic injection, subcutaneous injection, intravenous injection or perfusion. Pharmaceutical compositions suitable for injectable use or perfusion include sterile aqueous solutions or dispersions. Further, a preservative can be included to prevent the growth of microorganisms. A pharmaceutical composition may be formulated as a sterile, injectable solution for parenteral administration. Preferably, the pharmaceutical composition is administered as an intravitreal injection, subcutaneous injection, intravenous injection or perfusion. A nutritional composition preferably is formulated for oral application.

The pharmaceutical or nutritional composition apart from 6'-sialyllactose as an active ingredient preferably further comprises a pharmaceutically and/or nutritional acceptable carrier. The 6'-sialyllactose can be dissolved or dispersed in the pharmaceutically and/or nutritional acceptable carrier. The term "pharmaceutical and/or nutritional acceptable" refers to molecular entities and compositions that do not produce an adverse, allergic or other untoward reaction when administered to a subject, such as, for example, a human, as appropriate. The pharmaceutical and/or nutritional acceptable carrier can be, for example, a solid, liquid, or gas. Suitable carriers and adjuvants can be solid or liquid and correspond to the substances ordinarily employed in formulation technology for pharmaceutical formulations. Examples of solid carriers include lactose, terra alba, sucrose, talc, gelatine, agar, pectin, acacia, magnesium stearate, and stearic acid. Examples of liquid carriers are sugar syrup, peanut oil, olive oil, and water. Examples of gaseous carriers include carbon dioxide and nitrogen. The pharmaceutical compositions may be conveniently presented in unit dosage form and prepared under sterile conditions using standard pharmaceutical techniques well known in the art of pharmacy.

The present invention also relates to the use of 6'-sialyllactose and/or pharmaceutically acceptable salts thereof in the treatment of a disease selected from hearing loss and hearing loss-associated tinnitus.

A further aspect of the present invention relates to a method of treating a disease selected from hearing loss and hearing loss-associated tinnitus, the method comprising the step of administering to a subject in need thereof a therapeutically effective amount of 6'-sialyllactose and/or pharmaceutically acceptable salts thereof.

In embodiments, the disease is selected from acquired hearing loss and acquired hearing loss-associated tinnitus, preferably from acquired, non-infectious hearing loss and acquired, non-infectious hearing loss-associated tinnitus. In preferred embodiments, the acquired, non-infectious hearing loss is selected from the group comprising age-related hearing loss, noise-induced hearing loss and drug-induced hearing loss. Drug-induced hearing loss preferably is selected from antibiotic-induced hearing loss, chemotherapy-induced hearing loss, loop diuretic-induced hearing loss and aspirin-induced hearing loss.

The 6'-sialyllactose may be present in the form of the free or glycosidically unbound form. In further embodiments, the 6'-sialyllactose may be glycosidically bound to at least one sugar selected from the group comprising glucose, N-acetylglucosamine, N-acetylgalactosamine, galactose, fucose, mannose and xylose. The 6'-sialyllactose may be administered comprised in a pharmaceutical or nutritional composition.

The term "therapeutically effective amount" is used herein to mean an amount or dose sufficient to achieve a desired biological effect, for example an amount that is effective to improve signs or symptoms of hearing loss due to a cochlear disorder, for example by increasing the ability of the subject to hear or by preventing the subject's hearing from decreasing, or both.

Subjects include both human subjects and animal subjects, particularly mammalian subjects such as humans, particularly adult humans.

Unless otherwise defined, the technical and scientific terms used herein have the same meaning as commonly understood by one of ordinary skill in the art to which this invention belongs.

The examples, which follow, serve to illustrate the invention in more detail but do not constitute a limitation thereof.

The figures show:

FIG. 1A shows a representative image of an immunohistochemical staining against the mononuclear phagocyte marker CD68 in the spiral ganglion of the auditory system of a vehicle control PBS-treated mouse. Scale bar: 50 µm. In FIG. 1B the quantification of CD68+ cells per area in mice treated with either neomycin (Neo), neomycin plus 6'-sialyllactose (Neo+6SL) or vehicle control (PBS) revealed that neomycin treatment strongly increases the number of mononuclear phagocytes in the spiral ganglion. Data are shown as mean+SD of at least six images per mouse. Data were analyzed by one-way ANOVA with Bonferroni post-hoc correction ($*p<0.05$).

FIG. 2A shows a representative image of an immunohistochemical staining against the hair cell marker Myosin7a (Myo7a; upper image) and the nuclear marker 4',6-Diamidin-2-phenylindol (DAPI; lower image). The arrows indicate exemplary cells of the outer hair cells (left arrows) and of the inner hair cells (right arrows) and their respective staining. Scale bar: 20 µm. In FIG. 2B the quantification of Myo7A-positive hair cells of the middle turn of the cochlear organ of Corti of mice treated with either neomycin (Neo), neomycin plus 6'-sialyllactose (Neo+6SL) or vehicle control (PBS) revealed a strong reduction after neomycin treatment that was partially rescued by simultaneous treatment with 6'-sialyllactose. The mean hair cell number (Myo7A+ cells) per slice+SD of at least five images per mouse are shown. Data were analyzed by Kruskal-Wallis test with Dunn's multiple comparison test (**$p<0.01$; *$p<0.05$).

FIG. 3A shows a representative image of an immunohistochemical staining against the neuronal nuclei marker (NeuN) in the spiral ganglion of the auditory system of a vehicle control PBS-treated mouse. Scale bar: 50 µm. In FIG. 3B the quantification of NeuN-positive cells in mice treated with either neomycin (Neo), neomycin plus 6'-sialyllactose (Neo+6SL) or vehicle control (PBS) revealed a reduction after neomycin treatment that was less present by simultaneous treatment with 6'-sialyllactose. Data are shown as mean+SD of at least seven images per mouse. Data were analyzed by one-way ANOVA with Bonferroni post-hoc correction (*$p<0.05$).

Figure 4:
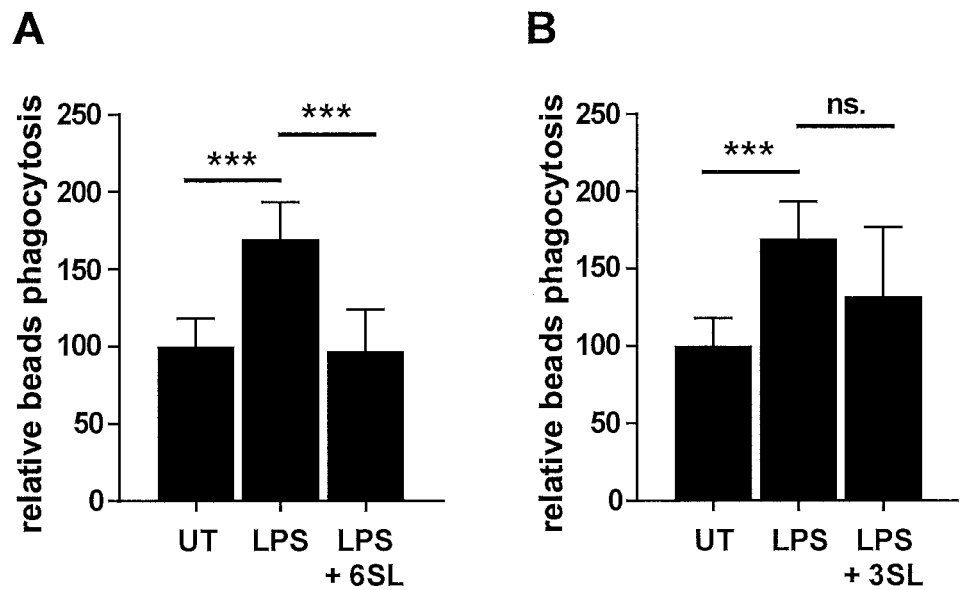

FIG. 4 shows the relative beads phagocytosis rate of human THP-1 macrophages treated with lipopolysaccharides (LPS), and additional treatment with 0.5 µM 6'-sialyllactose (LPS+6SL; FIG. 4A) or 0.5 µM 3'-sialyllactose (LPS+3SL; FIG. 4B) compared to untreated control (UT). Data are presented as mean+SD of at least six experiments. Data were analysed using one-way ANOVA with Bonferroni post-hoc correction (***$p<0.001$; ns.=not significant).

FIG. 5A shows a representative image of an immunohistochemical staining against neurofilament. Scale bar: 50 µm. In FIG. 5B the relative neural branches length in co-cultures of only neurons (neurons), neurons plus macrophages (neurons+THP1), neurons plus 6'-sialyllactose (neurons+6SL) and neurons plus macrophages plus 6'-sialyllactose (neurons+THP1+6SL) revealed that additional 6'-sialyllactose treatment could prevent the reduction in neural branches length. Data are presented as mean+SD of at least six images and were analysed using one-way ANOVA with Bonferroni post-hoc correction (*$p<0.05$; ***$p<0.001$).

EXAMPLE 1

Effect of 6'-sialyllactose on Macrophage Activation in the Inner Ear in an Animal Model of Antibiotic-Induced Hearing Loss To determine the effect of 6'-sialyllactose on macrophage activation in the inner ear, one-week old C57BL/6 pubs of mice were treated subcutaneously with either 50 µl PBS, 50 µl of 200 mg/kgbw neomycin (Neo, Sigma, N5285) in PBS, or 50 µl of 200 mg/kgbw neomycin (Sigma, N5285) plus 100 mg/kgbw 6'-sialyllactose (Carbosynth, OS04398) in PBS or only PBS as vehicle control for seven consecutive days. Mice were sacrificed two weeks after the last injection.

For further investigations, cochleae of the mice were isolated, post-fixed in 4% paraformaldehyde (PFA), decalcified in 5% EDTA, incubated in 30% sucrose until fully soaked, embedded in a cryoprotectant and cut into 20 µm thin slices from the apex to the base of the cochlea with a cryostat. For quantification of the macrophage activation in the cochlea, cryosections from different levels of the cochlea were chosen and co-stained with antibodies against the macrophage activation marker CD68 and the cellular nuclei marker DAPI. Z-stacks of 3×2 µm images were taken with a confocal microscope and Z-stacks were afterwards combined to maximal projection images. The area of the spiral ganglion was selected and measured using ImageJ. The CD68-positive cells were counted within the chosen area and the cell density of the macrophage in the spiral ganglion was calculated and normalized to the PBS vehicle treated condition. Data were analyzed by one-way ANOVA with Bonferroni post-hoc correction.

FIG. 1A shows a representative image of an immunohistochemical staining against the mononuclear phagocyte marker CD68 in the spiral ganglion of the auditory system of a vehicle control PBS-treated mouse. The measured area of the spiral ganglion is marked. The scale bar represents 50 µm. The area of the spiral ganglion was measured and the CD68+ cells in this area were counted. FIG. 1B shows the quantification of CD68+ macrophages per area in mice treated with neomycin (Neo), neomycin plus 6'-sialyllactose (Neo+6SL) or vehicle control (PBS). As can be taken from FIG. 1B, a slight attenuation of macrophage activation after treatment with 6'-sialyllactose was detected.

This illustrates that the antibiotic-induced activation of CD68+ phagocytes in the spiral ganglion of the auditory system of mice might partially be prevented by a treatment using subcutaneous application of 6'-sialyllactose.

Example 2

Effect of 6'-sialyllactose on Hair Cells in the Inner Ear in an Animal Model of Antibiotic-Induced Hearing Loss One-week old BL6 pubs of mice were treated subcutaneously with either 50 µl PBS, 50 µl of 200 mg/kgbw neomycin (Sigma, N5285) in PBS, or 50 µl of 200 mg/kgbw neomycin (Sigma, N5285) plus 100 mg/kgbw 6'-sialyllactose (Carbosynth, OS04398) in PBS for seven consecutive days. Mice were sacrificed two weeks after the last injection. For further investigations cochlea of the mice were isolated, post-fixed in 4% PFA, decalcified in 5% EDTA, incubated in 30% sucrose until fully soaked, embedded in a cryoprotectant and cut into 20 µm thin slices from the apex to base of the cochlea with a cryostat. For quantification of the hair cell density in the cochlea, cryosections from different levels of the cochlea were chosen and co-stained with antibodies against the hair cell marker Myosin7A (Myo7A) and the cellular nuclei marker DAPI. Images were taken with a confocal microscope and divided into different sections from apex to base of the cochlea. Myosin7a-positive cells were counted in each section.

FIG. 2A shows a representative image of an immunohistochemical staining against the hair cell marker Myosin7a and a co-staining with the nuclear marker DAPI. Scale bar: 20 µm. FIG. 2B shows the quantification of Myo7A-positive cells of the middle turn of the cochlea per slice of the mice treated with neomycin (Neo), neomycin plus 6'-sialyllactose (Neo+6; SL) or vehicle control (PBS). Data are shown as mean+SD of at least five images per mouse. Data were analyzed by Kruskal-Wallis test with one-way ANOVA with Dunn's multiple comparison test (**$p<0.01$; *$p<0.05$).

Figure 2:
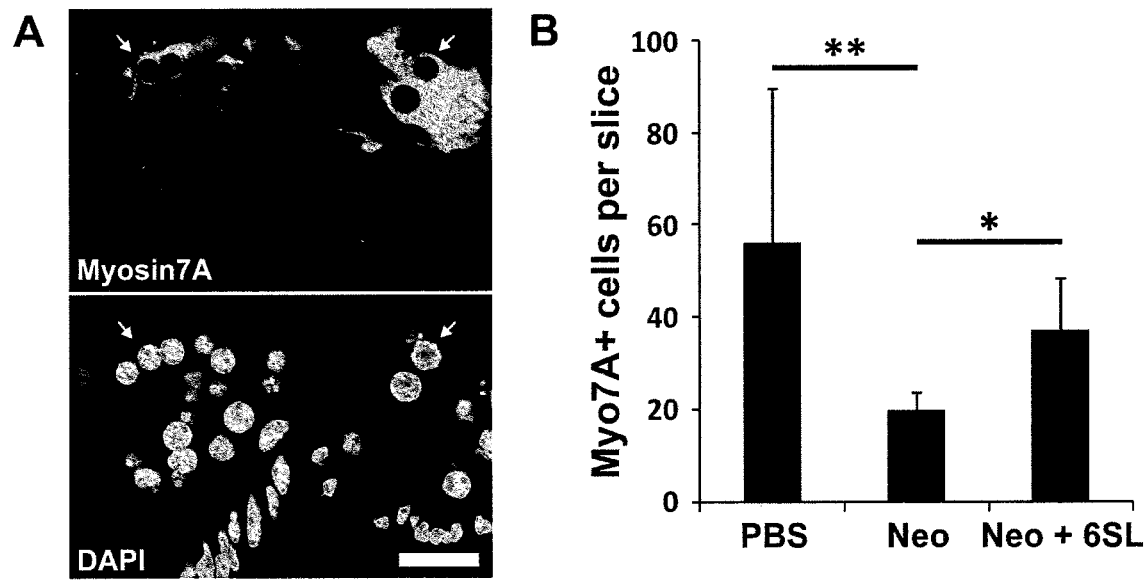

As can be taken from FIG. 2, the subcutaneous application of 6'-sialyllactose reduced the neomycin-induced loss of the hair cells in the middle turn of the cochlea of the mice.

Example 3

Effect of 6'-sialyllactose on Sensory Neurons of the Inner Ear in an Animal Model of Antibiotic-Induced Hearing Loss One-week old C57BL/6 pubs of mice were treated subcutaneously with either 50 µl PBS, 50 µl of 200 mg/kgbw neomycin (Sigma, N5285) in PBS, or 50 µl of 200 mg/kgbw neomycin (Sigma, N5285) plus 100 mg/kgbw 6'-sialyllactose (Carbosynth, OS04398) in PBS for seven consecutive days. Mice were sacrificed 2 weeks after the last injection. For further investigations cochlea of the mice were isolated, post-fixed in 4% PFA, decalcified in 5% EDTA, incubated in 30% sucrose until fully soaked, embedded in a cryoprotectant and cut into 20 μm thin slices from the apex to base of the cochlea with a cryostat. For quantification of the sensory neurons in the cochlea, cryosections from different levels of the cochlea were chosen and stained with antibodies for neuronal nuclei (NeuN) and the cellular nuclei marker DAPI. Z-stacks of 3×2 μm images were taken with a confocal microscope and stacks were afterwards combined to maximal projection images. The area of the spiral ganglion was selected and measured using ImageJ.

Figure 3:
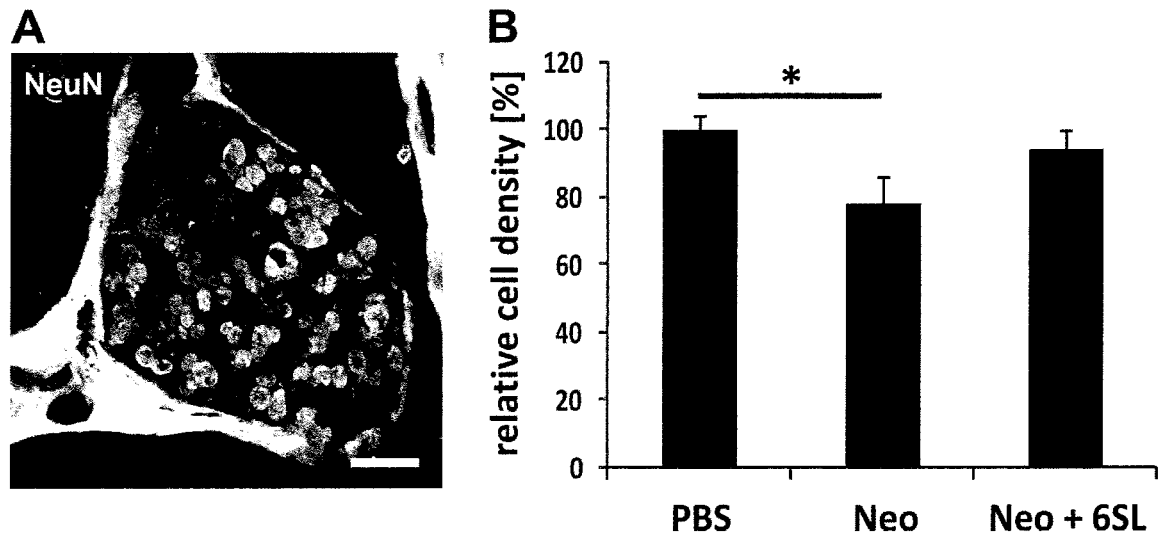

The NeuN-positive cells of the mice treated with neomycin (Neo), neomycin plus 6'-sialyllactose (Neo+6SL) or vehicle control (PBS) within the chosen area were counted and the neuronal density of the spiral ganglion was calculated and normalized to the PBS treated condition. FIG. 3 shows a representative image of an immunohistochemical staining against the neuronal nuclei marker (NeuN) in the spiral ganglion of the auditory system of a vehicle control PBS-treated mouse (Scale bar: 50 μm) in FIG. 3A and the quantification of NeuN-positive cells in FIG. 3B. Data are shown as mean+SD of at least seven images per mouse. Data were analyzed by one-way ANOVA with Bonferroni post-hoc correction ($*p<0.05$).

As can be taken from FIG. 3, 6'-sialyllactose might reduce the neomycin-induced loss of the sensory neurons in the spiral ganglion of the auditory system of the mice.

Example 4

Comparison of the Effect of 6'-sialyllactose and 3'-sialyllactose on Beads Phagocytosis in Human Macrophages The effect of 6'- and 3'-sialyllactose on beads phagocytosis was determined in the human mononuclear phagocyte cell line THP-1. The human mononuclear phagocyte cell line THP-1 was maintained in RPMI medium supplemented with 1% L-glutamine, 1% Penicillin/Streptomycin and 1% heat-inactivated chicken serum, at 5% CO2 and 37° C. For passaging, the cells were transferred to a 50 mL Falcon tube and centrifuged at 1300 rpm for 3 min. The supernatant was removed and the pellet was re-suspended in 5 mL of warm medium. For differentiation into macrophage-like cells, the cell density was adjusted to approximately $1\times10^6$ cells/mL. The cell suspension was mixed with 10 ng/mL PMA (Phorbol 12-myristate 13-acetate, Sigma) and distributed in volumes according to each experiment. Cells were incubated for 48 h, washed twice with medium and then cultured in medium for additional 48 h without PMA. For experimentation THP-1 macrophages were cultured in RPMI medium supplemented with 1% L-glutamine, 1% Penicillin/Streptomycin and 1% heat-inactivated chicken serum, at 5% CO2 and 37° C. Cells were treated for 24 hours with lipopolysaccharide LPS (3 μg/mL LPS, *E. coli* 0111:B4 strain InvivoGen, Germany) or LPS plus 0.5 mM of 6'-sialyllactose (Carbosynth) or 3'-sialyllactose (Carbosynth) that was re-purified by a HPLC-based anion exchange chromatography before use.

For analysis of beads phagocytosis, beads (microbeads from Polyscience Inc., PE labeled, 1 μm bead diameter; nanobeads from Life technologies, yellow-green labeled, 0.04 μm bead diameter) were added in a concentration of 1 μl beads/ml medium (microbeads) for 1 hour before analysis to the cells. For analysis, media was removed and cells were treated for 1-2 minutes with trypsin (Gibco) in order to get rid of beads sticking to the surface of macrophage cells. Afterwards cells were washed 3-times with PBS before being detached mechanically. Flow cytometry analysis was performed with a FACS Calibur (BD Biosciences).

Beads phagocytosis was analyzed by flow cytometry (BD FACSCalibur) by quantification of the percentage of cells having ingested 2 or more beads.

The FIG. 4 illustrates the phagocytosis of beads in THP-1 macrophages activated by 3 μg/ml lipopolysaccharides (LPS), and LPS-activated macrophages treated with 0.5 μM 6'-sialyllactose (LPS+6SL) and 3'-sialyllactose (LPS+3SL) compared to untreated controls in FIGS. 4A and 4B, respectively. Data are presented as mean+SD and were analyzed using one-way ANOVA with Bonferroni post-hoc correction ($***p<0.001$).

As can be taken from FIG. 4A, the activation of human THP-1 macrophages by treatment with lipopolysaccharides (LPS) increased the uptake of beads, while additional treatment with 0.5 μM 6'-sialyllactose (LPS+6SL) reduced the phagocytic uptake of microsphere beads. A comparison with FIG. 4B shows that treatment with 3'-sialyllactose (3SL) had no effect on the LPS-induced uptake of beads at the relative low concentration of 0.5 μM.

This shows that 0.5 μM 6'-sialyllactose reduced phagocytosis of beads in lipopolysaccharide-activated human THP-1 macrophages, while 3'-sialyllactose only showed a tendency without significance to reduce LPS-triggered uptake of beads at this relative low concentration.

Example 5

Effect of 6'-sialyllactose on Sensory Neural Branches Removal Mediated by Human THP1-Macrophages The effect of 6'-sialyllactose on sensory neural branches was determined in a human co-culture system with induced pluripotent stem cell derived sensory neurons and human THP1-macrophages.

Human sensory neurons were obtained from human induced pluripotent stem (iPS) cells. At day 0, the iPS colonies were detached by collagenase IV, collected by sedimentation, and resuspended in DMEM/F12 medium supplemented by 20% KO serum, 1% nonessential amino acids, 10 μM SB (SB-431542, inhibitor of TGF-beta), 1 μM dorsomorphin, 3 μM CHIR, and 0.5 μM purmorphamine for 2 days. At day 2, the medium was replaced to 50:50 DMEM/F12: neurobasal, 1:200 N2 supplement, 1:100 B27 supplement (N2B27 medium) supplemented with 10 μM SB, 1 μM dorsomorphin, 3 μM CHIR, and 0.5 M purmorphamine for 2 days. At day 4, 150 μM ascorbic acid was added to the above described N2B27 medium, but SB and dorsomorphin were withdrawn. At day 6, embryonic bodies were triturated and seeded on Geltrex-coated plates in low density and expand in N2B27 medium supplemented with CHIR, ascorbic acid, and purmorphamine for five passage numbers. Afterwards, the neural stem cells (NSCs) were ready for differentiation. For differentiation, NSCs were splitted by accutase and replated in Geltrex-coated plates. NSCs treated for two days with N2B27 medium supplemented by 3 μM CHIR, afterwards for one week with 10 ng/ml BMP4. Consequently, the pre-mature neurons were splitted by accutase and replated in a density of 20000 cells per well in Geltrex-coated chamber slides in N2B27 maturation medium contains 10 ng/ml BDNF, 10 ng/ml GDNF, and 500 μM dbcAMP for two weeks.

The human THP1 mononuclear phagocyte cell line was maintained in RPMI medium supplemented with 1% L-glutamine, 1% Penicillin/Streptomycin, 1% sodium-pyruvate, 1% heat-inactivated chicken serum, and 1% N2 supplement at 5% CO2 and 37° C. For passaging, the cells were transferred to a 50 mL Falcon tube and centrifuged at 1300 rpm for 3 min. The supernatant was removed and the pellet was re-suspended in 5 mL of warm medium. For differentiation into macrophage-like cells, the cell density was adjusted to approximately $1\times10^6$ cells/mL. Furthermore, the cell suspension was mixed with 10 ng/mL PMA and distributed in volumes according to each experiment. Cells were incubated for 48 h, washed twice with medium and then incubated for additional 48 h without PMA. For experiments, THP-1 macrophages were scraped, counted and added to the sensory iPS cell-derived neurons in co-culture medium 1:1 ratio (N2B27 medium plus BDNF, GDNF, dbcAMP) and treated with 100 µM 6'-sialyllactose (Carbosynth), that was re-purified by a HPLC-based anion exchange chromatography before use, or vehicle control for another 48 hours.

The co-culture were washed once with 1×PBS, and fixed with 4% paraformaldehyde (PFA) for 15 min at room temperature (RT). Then, unspecific binding sites of the fixed co-culture were blocked, and the co-culture was stained with rabbit anti-neurofilament and rat anti-CD11b specific antibodies and incubated overnight in 4° C. Next day, chambers containing the fixed co-culture were washed 3 times with blocking solution and incubated in secondary antibodies (Alexa488-conjugated anti-rabbit antibody and Cy3-conjugated anti-rat antibody) for 2 hours at RT. Then, the chambers were washed 3 times with 1×PBS, stained with the blue fluorescent nuclear dye DAPI and mounted. Pictures were taken by confocal microscope and neurite lengths were measured by NeuronJ plugin of ImageJ software.

Figure 5:
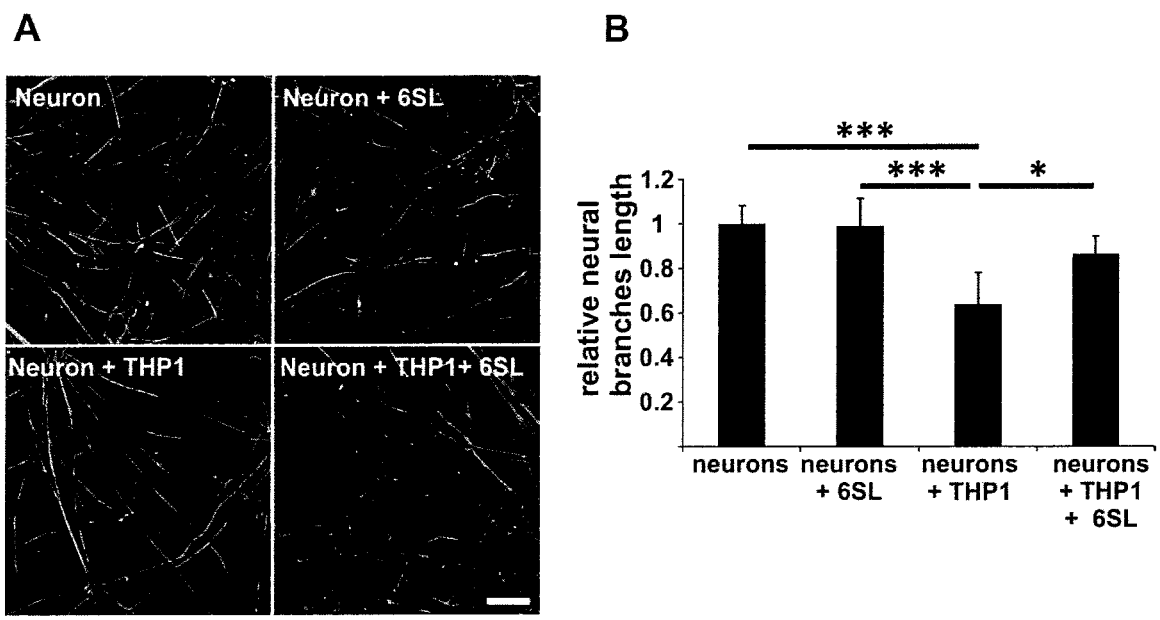

The relative neural branches length in co-cultures of only neurons (neurons), neurons plus macrophages (neurons+THP1), neurons plus 6'-sialyllactose (neurons+6SL) and neurons plus macrophages plus 6'-sialyllactose (neurons+THP1+6SL) was quantified and are shown in FIG. 5. Data are presented as mean+SD of at least six images and were analyzed using one-way ANOVA (Bonferroni); *, $p<0.05$; ***, $p<0.001$. As can be seen in FIG. 5, the addition of THP1 macrophages reduced the relative neural branches length and incubation with 6'-sialyllactose was able to protect the loss of neural branches length induced by the THP1 macrophages.

This shows that 6'-sialyllactose also protects human sensory neurons against neural branches removal mediated by human macrophages.

In summary, these experiments show that 6'-sialyllactose reduced neomycin-induced loss of hair cells in the cochlea and also slightly reduced neomycin-induced loss of sensory neurons in the spiral ganglion of mice. This shows that 6'-sialyllactose is usable for the treatment of acquired hearing loss in an animal model in vivo. Further, 6'-sialyllactose prevented the loss of neurites of sensory neurons mediated by macrophages in a human co-culture system.

The invention claimed is:

1. A method of treating a disease selected from hearing loss and hearing loss-associated tinnitus comprising administering to a mammal a pharmaceutical or nutritional composition comprising 6'-sialyllactose or pharmaceutically acceptable salts thereof, wherein the 6'-sialyllactose is free or glycosidically bound to at least one sugar selected from the group consisting of glucose, N-acetylglucosamine, N-acetylgalactosamine, galactose, fucose, mannose and xylose.

2. The method of claim 1, wherein the hearing loss or hearing loss-associated tinnitus is acquired hearing loss or acquired hearing loss-associated tinnitus.

3. The method of claim 2, wherein the hearing loss or hearing loss-associated tinnitus is acquired non-infectious hearing loss or acquired, non-infectious hearing loss-associated tinnitus.

4. The method of claim 3, wherein the acquired non-infectious hearing loss is selected from the group consisting of age-related hearing loss, noise-induced hearing loss and drug-induced hearing loss.

5. The method of claim 4, wherein the drug-induced hearing loss is selected from the group consisting of antibiotic-induced hearing loss, chemotherapy-induced hearing loss, loop diuretic-induced hearing loss and aspirin-induced hearing loss.

6. The method of claim 1, wherein the composition is a glycan composition containing 6'-sialyllactose or is a human milk oligosaccharide composition containing 6'-sialyllactose.

7. The method of claim 1, wherein the mammal is a human.

8. The method of claim 7, wherein the mammal is a human.

9. A method of treating a disease selected from hearing loss and hearing loss-associated tinnitus comprising administering to a mammal a pharmaceutical or nutritional composition comprising 6-sialyllactose or pharmaceutically acceptable salts thereof as an active ingredient, wherein the 6'-sialyllactose is free or glycosidically bound to at least one sugar selected from the group consisting of glucose, N-acetylglucosamine, N-acetylgalactosamine, galactose, fucose, mannose and xylose.

10. The method of claim 7, wherein the hearing loss or hearing loss-associated tinnitus is acquired hearing loss or acquired hearing loss-associated tinnitus.

11. The method of claim 9, wherein the hearing loss or hearing loss-associated tinnitus is acquired non-infectious hearing loss or acquired, non-infectious hearing loss-associated tinnitus.

12. The method of claim 10, wherein the acquired non-infectious hearing loss is selected from the group consisting of age-related hearing loss, noise-induced hearing loss and drug-induced hearing loss.

13. The method of claim 11, wherein the drug-induced hearing loss is selected from the group consisting of antibiotic-induced hearing loss, chemotherapy-induced hearing loss, loop diuretic-induced hearing loss and aspirin-induced hearing loss.

14. The method of claim 7, wherein the composition is a glycan composition containing 6'-sialyllactose or is a human milk oligosaccharide composition containing 6'-sialyllactose.

15. A method of treating a disease selected from hearing loss and hearing loss-associated tinnitus, the method comprising the step of administering to a subject in need thereof a therapeutically effective amount of 6'-sialyllactose and/or pharmaceutically acceptable salts thereof.

* * * * *